United States Patent
Furst et al.

(10) Patent No.: US 7,211,108 B2
(45) Date of Patent: May 1, 2007

(54) VASCULAR GRAFTS WITH AMPHIPHILIC BLOCK COPOLYMER COATINGS

(75) Inventors: Joseph G. Furst, Lyndhurst, OH (US); William Brodbeck, South Euclid, OH (US)

(73) Assignee: ICON Medical Corp., Cleveland, OH (US)

( * ) Notice: Subject to any disclaimer, the term of this patent is extended or adjusted under 35 U.S.C. 154(b) by 0 days.

(21) Appl. No.: 10/763,493

(22) Filed: Jan. 23, 2004

(65) Prior Publication Data

US 2005/0165476 A1  Jul. 28, 2005

(51) Int. Cl.
*A61F 2/06* (2006.01)

(52) U.S. Cl. .................... 623/1.44; 428/36.9; 623/1.46

(58) Field of Classification Search ............. 428/423.1, 428/36.9; 514/352, 423.7; 427/2.1; 66/108; 623/1.41–1.48, 1.49–1.54
See application file for complete search history.

(56) References Cited

U.S. PATENT DOCUMENTS

| | | | |
|---|---|---|---|
| 4,733,665 A | 3/1988 | Palmaz | |
| 4,776,337 A | 10/1988 | Palmaz | |
| 4,888,389 A | 12/1989 | Kennedy et al. | |
| 4,942,204 A | 7/1990 | Kennedy | |
| 5,024,671 A * | 6/1991 | Tu et al. .................... | 623/1.54 |
| 5,037,392 A | 8/1991 | Hillstead | |
| 5,051,272 A | 9/1991 | Hermes et al. | |
| 5,073,381 A | 12/1991 | Ivan et al. | |
| 5,108,424 A | 4/1992 | Hoffman, Jr. et al. | |
| 5,116,318 A | 5/1992 | Hillstead | |
| 5,180,366 A | 1/1993 | Woods | |
| 5,185,408 A | 2/1993 | Tang et al. | |
| 5,197,977 A | 3/1993 | Hoffman, Jr. et al. | |
| 5,246,451 A | 9/1993 | Trescony et al. | |
| 5,246,452 A | 9/1993 | Sinnott | |
| 5,283,257 A | 2/1994 | Gregory et al. | |
| 5,304,121 A | 4/1994 | Sahatjian | |
| 5,370,681 A | 12/1994 | Herweck | |
| 5,383,925 A | 1/1995 | Schmitt | |

(Continued)

FOREIGN PATENT DOCUMENTS

WO  WO 99/18998 A2  4/1999

OTHER PUBLICATIONS

Abstract of *Pharmacological Properties of Trapidil: Comparison with Other Coronary Vasodilators*, Ohnishi H, Kosuzume H, Yamaguchi K, Sato M, Umehara S, Funato H, Itoh C, Suzuki K, Kitamura Y, Suzuki Y, Itoh R., Nippon Yakurigaku Zasshi. Sep. 1980;76(6):495-503.

(Continued)

*Primary Examiner*—Suzette Gherbi
(74) *Attorney, Agent, or Firm*—Fay Sharpe LLP; Brian E. Turung

(57) ABSTRACT

One aspect of the invention relates to a graft, a surface of which is coated with an amphiphilic block copolymer that includes both hydrophobic and hydrophilic polymer chains. An amphiphilic block copolymer coating according to the invention can serve as a carrier for a very broad range of drugs, possibly including every drug presently used, being considered for use, or likely to be used in the future to inhibit stenosis. The release rates of the drugs can be controlled, for example, through the length of the polymer chains, through their ratio, or through the degree of cross-linking.

55 Claims, 1 Drawing Sheet

U.S. PATENT DOCUMENTS

| | | | |
|---|---|---|---|
| 5,383,927 | A | 1/1995 | De Goicoechea et al. |
| 5,383,928 | A | 1/1995 | Scott et al. |
| 5,417,981 | A | 5/1995 | Endo |
| 5,449,382 | A | 9/1995 | Dayton |
| 5,464,650 | A | 11/1995 | Berg et al. |
| 5,500,013 | A | 3/1996 | Buscemi et al. |
| 5,516,781 | A | 5/1996 | Morris et al. |
| 5,545,208 | A | 8/1996 | Wolff et al. |
| 5,563,146 | A | 10/1996 | Morris et al. |
| 5,578,075 | A | 11/1996 | Dayton |
| 5,605,696 | A | 2/1997 | Eury et al. |
| 5,609,629 | A | 3/1997 | Fearnot |
| 5,624,411 | A | 4/1997 | Tuch |
| 5,665,728 | A | 9/1997 | Morris et al. |
| 5,679,400 | A | 10/1997 | Tuch |
| 5,716,981 | A | 2/1998 | Hunter et al. |
| 5,733,925 | A | 3/1998 | Kunz et al. |
| 5,772,864 | A * | 6/1998 | M.o slashed.ller et al. ... 205/73 |
| 5,807,944 | A | 9/1998 | Hirt et al. |
| 5,811,447 | A | 9/1998 | Kunz et al. |
| 5,824,049 | A | 10/1998 | Ragheb |
| 5,873,904 | A | 2/1999 | Ragheb |
| 5,962,620 | A | 10/1999 | Reich et al. |
| 5,981,568 | A | 11/1999 | Kunz et al. |
| 5,993,972 | A * | 11/1999 | Reich et al. ............ 428/423.1 |
| 6,074,659 | A | 6/2000 | Kunz et al. |
| 6,096,070 | A | 8/2000 | Ragheb |
| 6,120,536 | A | 9/2000 | Ding et al. |
| 6,120,847 | A | 9/2000 | Yang et al. |
| 6,156,062 | A * | 12/2000 | McGuinness ............. 623/1.22 |
| 6,156,373 | A | 12/2000 | Zhong |
| 6,162,247 | A | 12/2000 | Weadock et al. |
| 6,171,609 | B1 | 1/2001 | Kunz |
| 6,200,589 | B1 | 3/2001 | Kennedy et al. |
| 6,200,960 | B1 | 3/2001 | Khachigian |
| 6,206,916 | B1 * | 3/2001 | Furst .......................... 623/1.46 |
| 6,221,099 | B1 * | 4/2001 | Andersen et al. .......... 623/1.15 |
| 6,245,537 | B1 | 6/2001 | Williams |
| 6,258,121 | B1 | 7/2001 | Yang et al. |
| 6,268,390 | B1 | 7/2001 | Kunz |
| 6,273,913 | B1 | 8/2001 | Wright et al. |
| 6,287,628 | B1 | 9/2001 | Hossainey et al. |
| 6,299,604 | B1 | 10/2001 | Ragheb |
| 6,306,421 | B1 | 10/2001 | Kunz et al. |
| 6,322,847 | B1 | 11/2001 | Zhong |
| 6,333,347 | B1 | 12/2001 | Hunter et al. |
| 6,356,600 | B1 | 3/2002 | Kirsteins |
| 6,358,989 | B1 | 3/2002 | Kunz |
| 6,365,171 | B1 | 4/2002 | Kennedy et al. |
| 6,368,658 | B1 | 4/2002 | Schwarz |
| 6,369,065 | B1 | 4/2002 | Chatelain |
| 6,379,379 | B1 | 4/2002 | Wang |
| 6,379,381 | B1 | 4/2002 | Hossainey et al. |
| 6,391,052 | B2 | 5/2002 | Buirge et al. |
| 6,436,133 | B1 | 8/2002 | Furst et al. |
| 6,491,938 | B2 | 12/2002 | Kunz et al. |
| 6,515,009 | B1 | 2/2003 | Kunz et al. |
| 6,517,571 | B1 * | 2/2003 | Brauker et al. ............ 623/1.13 |
| 6,528,584 | B2 | 3/2003 | Kennedy et al. |
| 6,530,951 | B1 | 3/2003 | Bates |
| 6,545,097 | B2 | 4/2003 | Pinchuk et al. |
| 6,555,157 | B1 | 4/2003 | Hossainey et al. |
| 6,555,619 | B1 | 4/2003 | Kennedy et al. |
| 6,569,195 | B2 | 5/2003 | Yang et al. |
| 6,569,441 | B2 | 5/2003 | Kunz |
| 6,583,251 | B1 | 6/2003 | Chaikof et al. |
| 6,585,764 | B2 | 7/2003 | Wright et al. |
| 6,599,275 | B1 | 7/2003 | Fischer |
| 6,599,928 | B2 | 7/2003 | Kunz et al. |
| 6,607,598 | B2 | 8/2003 | Schwarz |
| 6,623,521 | B2 | 9/2003 | Steinke |
| 6,624,138 | B1 | 9/2003 | Sung |
| 6,641,611 | B2 | 11/2003 | Jayaraman |
| 6,652,575 | B2 | 11/2003 | Wang |
| 6,656,506 | B1 | 12/2003 | Wu |
| 6,656,966 | B2 | 12/2003 | Garvey |
| 6,663,881 | B2 | 12/2003 | Kunz et al. |
| 6,695,833 | B1 | 2/2004 | Frantzen |
| 6,720,350 | B2 | 4/2004 | Kunz |
| 6,723,814 | B2 * | 4/2004 | Meier et al. ................ 526/279 |
| 6,726,923 | B2 | 4/2004 | Iyer et al. |
| 6,730,064 | B2 | 5/2004 | Ragheb |
| 6,730,349 | B2 | 5/2004 | Schwarz |
| 6,734,194 | B2 | 5/2004 | End |
| 6,743,805 | B2 | 6/2004 | End |
| 6,753,071 | B1 | 6/2004 | Pacetti |
| 6,759,431 | B2 | 7/2004 | Hunter |
| 6,770,729 | B2 | 8/2004 | Van Antwerp |
| 6,774,278 | B1 | 8/2004 | Ragheb et al. |
| 6,780,849 | B2 | 8/2004 | Herrmann |
| 6,783,793 | B1 | 8/2004 | Hossainy |
| 6,808,536 | B2 | 10/2004 | Wright |
| 6,852,353 | B2 * | 2/2005 | Qiu et al. .................. 427/2.24 |
| 7,160,592 | B2 * | 1/2007 | Rypacek et al. ........... 428/36.9 |
| 2002/0032414 | A1 | 3/2002 | Ragheb |
| 2002/0107330 | A1 | 8/2002 | Pinchuk et al. |
| 2003/0026840 | A1 | 2/2003 | Plank et al. |
| 2003/0028243 | A1 | 2/2003 | Bates |
| 2003/0028244 | A1 | 2/2003 | Bates |
| 2003/0036794 | A1 | 2/2003 | Ragheb |
| 2003/0040790 | A1 | 2/2003 | Furst |
| 2003/0064098 | A1 | 4/2003 | Kararli et al. |
| 2003/0083646 | A1 | 5/2003 | Sirhan et al. |
| 2003/0093141 | A1 | 5/2003 | Dimatteo et al. |
| 2003/0099712 | A1 | 5/2003 | Jayaraman |
| 2003/0158598 | A1 | 8/2003 | Ashton et al. |
| 2003/0199969 | A1 | 10/2003 | Steinke et al. |
| 2003/0216534 | A1 | 11/2003 | Chaikof et al. |
| 2003/0228364 | A1 | 12/2003 | Nathan |
| 2003/0229390 | A1 | 12/2003 | Ashton et al. |
| 2003/0229392 | A1 | 12/2003 | Wong |
| 2003/0229393 | A1 | 12/2003 | Kutryk et al. |
| 2004/0047909 | A1 | 3/2004 | Ragheb |
| 2004/0093076 | A1 | 5/2004 | White |
| 2004/0093077 | A1 | 5/2004 | White |
| 2004/0219223 | A1 | 11/2004 | Kunz |
| 2004/0243225 | A1 | 12/2004 | Ragheb |

OTHER PUBLICATIONS

Abstract of *Effects of Trapidil on Thromboxane A2-induced Aggregation of Platelets, Ischemic Changes in Heart and Biosynthesis of Thromboxane A2*, Ohnishi H, Kosuzume H, Hayashi Y, Yamaguchi K, Suzuki Y, Itoh R., Prostaglandins Med. Mar. 1981;6(3):269-81.

Abstract of *Antithromobitic Activity and the Mechanism of Action of Trapidil (Rocornal)*, Suzuki Y, Yamaguchi K, Shimada S, Kitamura Y, Ohnishi H., Prostaglandins Leukot Med. Dec. 1982;9(6):685-95.

Abstract of *Suppression of Fibroblast Proliferation In Vitro and of Myointimal Hyperplasia In Vivo by the Triazolopyrimidine, Trapidil*, Tiell ML, Sussman II, Gordon PB, Saunders RN, Artery. 1983;12(1):33-50.

*Influence of Cardiovascular Drugs on Platelet Aggregation*, Forster W, Block HU, Giessler C, Heinroth I, Mentz P, Ponicke K, Rettkowski W, Zehl U., : Adv Myocardiol. 1983;4:539-47.

Abstract of *Trapidil in Preventing Restenosis After Balloon Angioplasty in the Ather Osclerotic Rabbit*, MW Liu, GS Roubin, KA Robinson, AJ Black, JA Hearn, RJ Siegel, and SB King, 3d Circulation 1990 81: 1089-1093.

Abstract of *Effects of Trapidil (Triazolopyrimidine), a Platelet-Derived Growth Factor Antagonist, in Preventing Restenosis After Percutaneous Transluminal Coronary Angioplasty*, Okamoto S, Inden M, Setsuda M, Konishi T, Nakano T, Am Heart J. Jun. 1992;123(6):1439-44.

Abstract of *Trapidil (triazolopyrimidine), A Platelet-Derived Growth Factor Antagonist, Reduces Restenosis After Percutaneous Transluminal Coronary Angioplasty. Results of the Randomized, Double-Blind STARC Study. Studio Trapidil Versus Aspirin Nella Restenosi Coronarica*, A Maresta, M Balducelli, L Cantini, A Casari, R Chioin, M Fabbri, A Fontanelli, PA Monici Preti, S Repetto, and S De Serv, Circulation, Dec. 1994; 90: 2710-2715.

Abstract of *The Trapidil Restenosis Trial (STARC study): Background, Methods and Clinical Characteristics of the Patient Population*, Maresta A, Balducelli M, Cantini L, Casari A, Chioin R, Fontanelli A, Monici Preti PA, Repetto S, Raffaghello S.,Clin Trials Metaanal. Apr. 1994;29(1):31-40.

Abstract of *Fast and Reproducible Vascular Neointima Formation in the Hamster Carotid Artery: Effects of Trapidil and Captopril*, Matsuno H, Stassen JM, Hoylaerts MF, Vermylen J, Deckmyn H., Thromb Haemost. Dec. 1995;74(6):1591-6.

*New Aspects in Antithrombotic Therapy—Platelet Inhibitors-*, Terres W, Meinertz T., Herz. Feb. 1996;21(1):1-11.

*Management of restenosis after Coronary Intervention*, Dangas G, Fuster V., Am Heart J. Aug. 1996;132(2 Pt 1):428-36.

*Results of a Meta-Analysis of Trapidil, a PDGF Inhibitor Â A Sufficient Reason for a Second Look to the Pharmacological Approach to Restenosis*, Serruys PW, Banz K, Darcis T, Mignot A, van Es GA, Schwicker D., J Invasive Cardiol. Oct. 1997;9(8):505-512.

*A Randomized Comparison of Trapidil (triazolopyrimidine), a Platelet-Derived Growth Factor Antagonist, Versus Aspirin in Prevention of Angiographic Restenosis after Coronary Artery Palmaz-Schatz Stent Implantation*, Galassi AR, Tamburino C, Nicosia A, Russo G, Grassi R, Monaco A, Giuffrida G., Catheter Cardiovase Interv. Feb. 1999;46(2):162-8.

*Reference Chart Derived From Post-Stent-Implantation Intravascular Ultrasound Predictorsof 6-Month Expected Restenosis on Quantitative Coronary Angiography*, P. J. de Feyter, P. Kay, C. Disco, and P. W. Serruys, Circulation, Oct. 1999; 100: 1777-1783.

*Trapidil Inhibits Monocyte Chemoattractant Protein-1 and macrophage Accumulation After Balloon Arterial Injury in Rabbits*, Poon M, Cohen J, Siddiqui Z, et al., Lab Invest. 1999;79:1369-1375.

*The TRAPIST study—A multicentre randomized placebo controlled clinical trial of trapidil for prevention of restenosis after coronary stenting, measured by 3-D intravascular ultrasound*, P.W. Serruys, D.P. Foley, M. Pieper, J.A. de Feyter on behalf of the TRAPIST investigators, European Heart Journal (2001) 22, 1938-1947, doi:10.1053/euhj.2001.2627, available online at http://www.idealibrary.com.

* cited by examiner

VASCULAR GRAFTS WITH AMPHIPHILIC BLOCK COPOLYMER COATINGS

FIELD OF THE INVENTION

The present invention relates generally to the field of medicine and more particularly relates to drug coated vascular grafts.

BACKGROUND OF THE INVENTION

Vascular grafts are medical devices used as an artificial conduit for bodily fluids, usually blood. In hemodialysis, the vascular graft serves as a nonstatic reservoir of blood, where blood is readily accessible to a dialysis machine. The vascular graft serves as a life line, an essential interface between the patient and the dialysis machine. In the treatment of peripheral vascular disease and coronary artery disease, vascular grafts provide an artificial conduit bypassing or replacing diseased blood vessels.

Vascular grafts can be natural or artificial. In coronary artery disease, artificial vascular grafts are rarely used due to a high incidence of thrombosis either within the tubular structure or at the anastamosis site. The current graft material of choice is to use a native blood vessel such as the left internal mammary artery or saphenous vein.

In general, thrombosis is problematic with vascular grafts. Thrombosis or cellular growth is the main cause of stenosis within the internal lumen of the vascular graft. Stenosis can occurs as a result of the body's natural healing mechanism. When a vascular graft is implanted, injury occurs to the arterial or venous system to which the vascular graft is sutured and or attached. The vascular graft is also a foreign body. Through a complex process, smooth muscle cells, endothelial cells etc. migrate onto the internal lumen of the graft. As the smooth muscle cells proliferate, they form a neointimal hyperplasia. Over time the neointimal hyperplasia progresses, causing a reduction in the internal diameter of the internal lumen. Stenosis can also be caused by vascular narrowing.

There have been many attempts to inhibit stenosis and thrombosis. Anticoagulants such as heparin have been tried with little success. Antimicrotubule agents such as paclictaxel and docetaxel are known to inhibit mitosis and hence cellular proliferation. Antiproliferative agents such as cyclophosphamide, mithromycin, and actinomycin-D are known to prevent proliferation of smooth muscle cells. Sirolimus, cyclosporine A, dexamethasone and methyl prednisolone are immunosuppressive agents that have been shown to prevent or retard neointimal hyperplasia.

While drugs can significantly inhibit or prevent the occurrence of stenosis and thrombosis, the continued need for the drugs after a graft has been installed can require the patient to remain in a hospital for extended periods of time. It would be advantageous if these drugs could be released from a biocompatible polymer coating within a graft.

At present, there are many biocompatible polymers. For example, poly(ethylene glycol) (PEG) is a water soluble polymer showing excellent biocompatibility and has been frequently used in biomedical applications. Similarly, polysiloxanes are widely used in the biomedical field and have been the subject of intense study both in the academic field as well as in industry.

Amphiphilic polymer networks have also been identified as potentially useful biomaterials. Amphiphilic polymer networks are co-continuous assemblages of hydrophilic and hydrophobic polymer chains that are able to swell in both hydrophilic solvents (e.g., water) and hydrophobic solvents (e.g., a liquid hydrocarbon). Because these materials swell in water, they generally fall into a class of compounds known as "hydrogels".

The first amphiphilic membranes for biomaterials were developed over a decade ago. These were networks of hydrophilic polymers with the hydrophobic crosslinking agent, di-methacryl-telechelic polyisobutylene (MA-PIB-MA). Synthesis was accomplished by living carbocationic polymerization, which involves the free radical copolymerization and can use a variety of inexpensive, commercially available monomers, for example, N-dimethylaminoethyl methacrylate and dimethyl acrylamide.

Kennedy, U.S. Pat. No. 4,486,572 discloses the synthesis of styryl-telechelic polyisobutylene and amphiphilic networks comprising the copolymerization product of the styryl-telechelic polyisobutylene with vinyl acetate or N-vinyl-2-pyrollidone. Kennedy, U.S. Pat. No. 4,942,204 discloses an amphiphilic copolymer network swellable in both water and n-heptane but insoluble in either, comprising the reaction product of an acrylate or methacrylate of a dialkylaminoalkyl with a hydrophobic bifunctional acryloyl or methacryloyl capped polyolefin. The preferred embodiment disclosed is an amphiphilic network having been synthesized by the free-radical copolymerization of a linear hydrophobic acrylate (A-PIB-A) or methacrylate capped polyisobutylene (MA-PIB-MA) with 2-(dimethylamino)ethyl methacrylate (DMAEMA). In a continuation-in-part to U.S. Pat. No. 4,942,204, Ivan et al. U.S. Pat. No. 5,073,381 discloses various amphiphilic copolymer networks that are swellable in water and n-heptane that comprise the reaction product of a hydrophobic linear acryloyl- or methacryloyl-capped polyolefin and a hydrophilic polyacrylate or polymethacrylate, such as N,N-dimethylacrylamide (DMAAm) and 2-hydroxyethylmethyl methacrylate (HEMA).

Hirt, U.S. Pat. No. 5,807,944 discloses a copolymer of controlled morphology comprising at least one oxygen permeable polymer segment and at least one ion permeable polymer segment, wherein the oxygen permeable segments and the ion permeable segments are linked together through a non-hydrolysable bond. The oxygen-permeable polymer segments are selected from polysiloxanes, perfluoroalkyl ethers, polysulfones, and other unsaturated polymers. The ion permeable polymers are selected from cyclic imino ethers, vinyl ethers, cyclic ethers, including epoxides, cyclic unsaturated ethers, N-substituted aziridines, beta-lactones, beta-lactanes, ketene acetates, vinyl acetates and phosphoranes.

U.S. application Ser. No. 09/433,660 discloses an amphiphilic network comprising the reaction product of hydrophobic crosslinking agents and hydrophilic monomers wherein the hydrophobic crosslinking agents are telechelic three-arm polyisobutylenes having acrylate or methacrylate end caps and wherein the hydrophilic monomers are acrylate or methacrylate derivatives.

SUMMARY OF THE INVENTION

The following presents a simplified summary in order to provide a basic understanding of some aspects of the invention. This summary is not an extensive overview of the invention. It is intended neither to identify key or critical elements of the invention nor to delineate the scope of the invention. Rather, the primary purpose of this summary is to present some concepts of the invention in a simplified form as a prelude to the more detailed description that is presented later.

One aspect of the invention relates to a graft, a surface of which is coated with an amphiphilic block copolymer that includes both hydrophobic and hydrophilic polymer chains. An amphiphilic block copolymer coating according to the invention can be used to control the porosity of a graft and can itself be relatively inert biologically. The polymer coating can be flexible and stable under manipulation of the graft, including suturing. Significantly, the coating can serve as a carrier for a very broad range of drugs, possibly including every drug presently used, being considered for use, or likely to be used in the future to inhibit stenosis or thrombosis. The release rates of the drugs can be controlled, for example, through the length of the polymer chains, their ratio, or their degree of crosslinking.

Another aspect of the invention relates to a graft, a surface of which is coated with collagen containing a drug selected from the group consisting of stem cells, antibodies, genetic materials, and lymphokines. Collagen exhibits many desirable properties for carrying these types of drugs on a graft.

Other aspects of the invention relate to manufacturing amphiphilic block copolymer coated grafts. One of these aspects relates to polymerizing a solution containing monomers and a drug. Another of these aspects is a method of increasing the loading of a drug in an amphiphilic block copolymer through multiple cycles of swelling the polymer with a solvent drug solution, evaporating at least some of the solvent between cycles.

Grafts according to the invention are useful in treating vascular disease, including disease affecting small vessels and disease affecting coronary arteries. The delivery of drugs according to the invention can substantially reduce stenosis and thrombosis rates. In some instances, the effects of these treatments can be enhanced by oral administration of the drugs.

A further aspect of the invention relates to treatments wherein microparticles, especially microparticles of amphiphilic block copolymers, are used as carriers for drugs. The microparticles can be dispersed in a coating, such as a hydrogel, covering a surface of the graft.

To the accomplishment of the foregoing and related ends, the following description and annexed drawings set forth in detail certain illustrative aspects and implementations of the invention. These are indicative of but a few of the various ways in which the principles of the invention may be employed. Other aspects, advantages and novel features of the invention will become apparent from the following detailed description of the invention when considered in conjunction with the drawings.

DETAILED DESCRIPTION OF THE INVENTION

Figure 1:
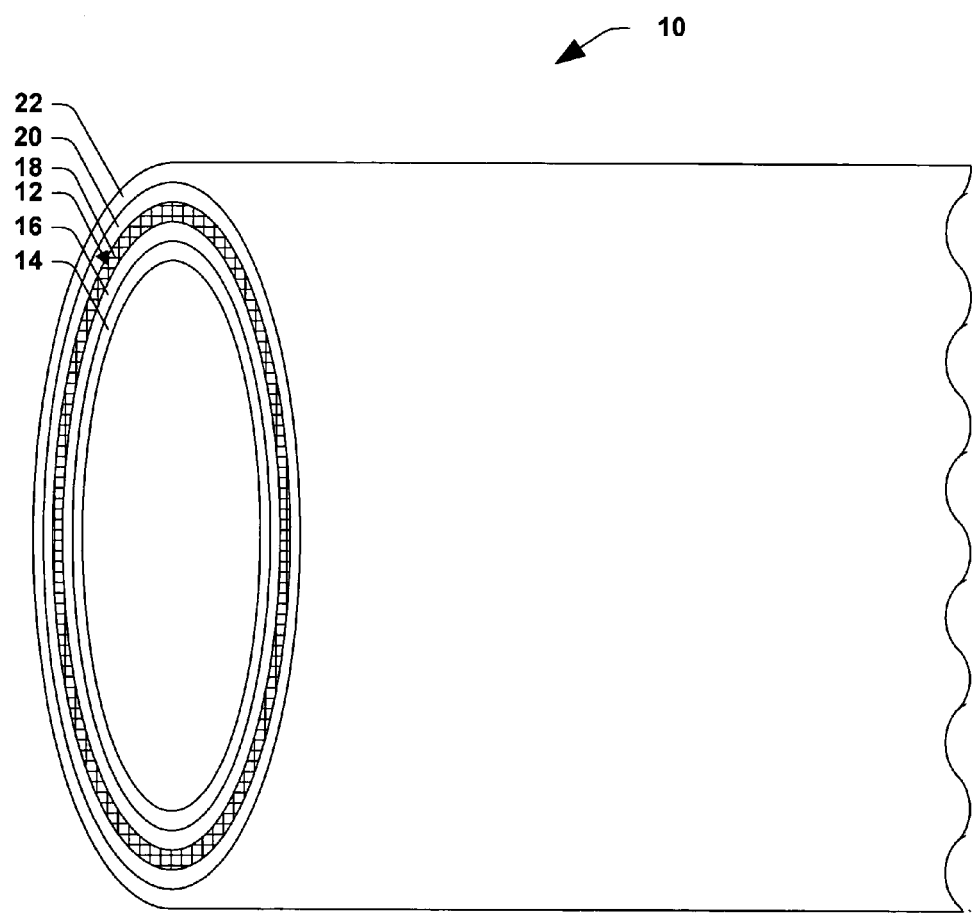
FIG. 1 is an illustration of one end of a graft coated by one or more polymer layers functionally divided into five layers for illustrative purposes.

An exemplary graft according to the invention includes a wall forming a lumen, an amphiphilic block copolymer coating a surface of the wall, and a drug carried by the polymer. The drug is of a type and is provided in an effective amount to significantly inhibit one or more of stenosis, vascular narrowing, and thrombosis. For purposes of this disclosure, stenosis encompasses vascular narrowing and restenosis and to inhibit means to slow the rate or reduce the occurrence of.

A graft of the present invention provides a versatile platform for on-graft drug delivery. The amphiphilic block copolymer can be stable and flexible, whereby it retains its integrity during and after installation. The polymer can have a high degree of bio- and hemo-compatibility and can carry virtually any drug that might be of interest in connection with grafts, including virtually any drug that is potentially useful in preventing graft stenosis or thrombosis. Release rates can be controlled as needed through variations in composition, loading, layering, and/or cross-linking.

While other graft/polymer combinations might have the features required for controlled release coatings of particular drugs on grafts, grafts according to the present invention have a significant advantage in versatility. Versatility is important in view of the need to conduct extensive testing prior to introducing any new material into the human body. A graft according to the present invention can easily, and with minimal testing, be adapted to implement advances in graft design and stenosis or thrombosis-preventing drug treatments.

The wall of the graft is generally in the shape of a simple tube, but can be of more complex shape as in a graft that repairs or replaces a branching vessel. Grafts having lumens with diameters of about 6 mm or greater are considered large. Grafts having lumens with diameters of about 5 mm or less are considered small. Typically, the graft is designed so that its open ends can be sutured to blood vessels in a living organism. A preferred graft is therefore stable under the physical manipulation involved in suturing.

The wall is typically made of a flexible fabric, although comparatively rigid materials, including metals and polymers, can also be used. Fabrics can be woven, knitted, braided, or nonwoven. Examples of fabrics include, polyester (PET), polytetrafluoroethylene (PTFE) (often expanded) (including Teflon and Dacron), and polyurethanes (including Lycra, Pellethane, and Biomer). Metals include stainless steel, zirconium, tantalum, titanium, tungsten, gold, platium, iridium, rhodium, nitinol, alloys thereof, and alloys of cobalt, nickel, chromium and molybdenum.

When the graft is made from a polymer, the polymer can be biostable or bioerodible. Examples of suitable biostable polymers include polyurethanes, polysilicones, poly(meth) acrylates, polyesters, polyalkyl oxides, polyvinyl alcohols, polyalkylene glycols and polyvinyl pyrrolidone. Examples of suitable bioerodible polymers include polymers of aliphatic polyesters, poly(amino acids), copoly(ether-esters), polyalkylenes oxalates, polyamides, poly(iminocarbonates), polyorthoesters, polyoxaesters, polyamidoesters, polyoxaesters containing amido groups, poly(anhydrides), polyphosphazenes, biomolecules and blends thereof.

The wall may be supported by a stent, especially when the wall is a fabric. A stent is a stiff yet flexible generally tubular structure. Typically, a stent can be enlarged under the pressure of an angioplasty balloon from a first diameter to a second diameter. Preferably the enlargement in diameter occurs with little or no axial lengthening. Once enlarged, the stent resists shrinkage. An expandable stent can have any suitable structure. Examples include frameworks of struts, slotted tubes, coiled helical wires, coiled sheets, and heat-expandable tubes. The stent can be formed by a process that includes a microelectromechanical machining process. The stent may include a ratcheting mechanism to prevent contraction following expansion. The ratcheting mechanism can include teeth or other indentations. The microelectromechanical machining process can be used to form the teeth or other indentations that are part of the ratcheting mechanism.

A stent is generally made of a metal, preferably stainless steel, but it can also be formed of a polymer, either biostable or bioerodable.

The graft, and any assoicated stent, may be provided with a biocompatible coating. Generally, an amphiphilic block copolymer coating will provide biocompatibility, but in some cases, for example where the amphiphilic polymer does not cover the entire surface, has slight instability, or has very large pores, it may be desireable to provide biocompatible coating beneath the amphiphilic block copolymer coating.

Any suitable biocompatible coating can be used. In one embodiment, the biocompatible coating includes a metal. A metal coating can include, for example, gold, platinum, titanium, nickel, tin, or a combination. In another embodiment, the biomechanical coating includes a polymer. The polymer can be, for example, polytetrafluoroethylene, polyethylene, poly(hydroxyethly methacrylate), poly(vinyl alcohol), polycaprolactone, poly(D, L-lactic acid), poly(L-lactic acid), poly(lactide-co-glycolide), poly(hydroxybutyrate), poly(hydroxybutyrate-co-valerate), polydioxanone, polyorthoester, polyanhydride, poly(glycolic acid), poly(glycolic acid-cotrimethylene cabonate), polyphosphoester, polyphosphoester urethane, poly(amino acids), cyanoacrylates, poly (trimethylene carbonate), poly(iminocarbonate), copoly (ether-esters), polyalkylene oxalates, polyphosphazenes, polyiminocarbonates, aliphatic polycarbonate, polyethylene oxide, polyethylene gylcol, poly(propylene oxide), polyacrylamide, polyacrylic acid (30-60% solution), polymethacrylic acid, poly(N-vinyl-2-pyrollidone), polyurethane, poly(aminoacid), cellulosic polymer (e.g. sodium carboxymethyl cellulose, hydroxyethyl celluslose), collagen, carrageenan, alginate, starch, dextrin, gelatin, poly (lactide), poly(glycolide), polydioxanone, polycaprolactone, polyhydroxybutyrate, poly(phospazazene), poly(phosphate ester), poly(lactide-co-glycolide), poly(glycolide-co-trimethylene carbonate), poly(glycolide-co-caprolactone), polyanhydride, polyamide, polyestes, polyether, polyketone, polyether elastomer, parylene, polyether amide elastomers, polyacrylate-based elastomer, polyethylene, polypropylene, and/or and derivatives thereof.

One important class of grafts and/or graft coatings forms a carpet-like surface. A carpet-like surface results when long chain molecules are bound at one end to the underlying stent surface. PTFE, for example, can provide a carpet-like surface. An amphiphilic block copolymer can fill or partially fill the interstices between long chain molecules and smooth over a carpet-like surface.

Various definitions of amphiphilic polymer are used in the literature. For purpose of the present disclosure, however, an amphiphilic polymer is a copolymer that includes both hydrophobic and hydrophilic polymer chains and is able to swell in both hydrophilic solvents (e.g., water) and hydrophobic solvents (e.g., n-heptane). This definition excludes, for example, a simple poly(ethylene glycol) polymer, which some have characterized as amphiphilic in view of its intermediate hydrophilicity.

Amphiphilic block copolymers include polymers having hydrophobic polymer chains crosslinked by hydrophilic polymer chains, polymers having hydrophilic polymer chains crosslinked by hydrophobic polymer chains, polymers having hydrophobic and hydrophilic polymer chains crosslinked by a crosslinking agent, and polymers in which hydrophobic and hydrophilic chains link end to end. Amphiphilic graft copolymers include polymers having a hydrophilic backbone to which hydrophobic chains are attached and polymers having a hydrophobic backbone to which hydrophilic chains are attached. As the terms are used here, a graft copolymer is not, in general, a block copolymer.

The assemblages of polymer chains are generally random. Preferably, the polymer chains form a continuous network through either physical or chemical crosslinking. Physical crosslinking refers, for example, to bonding that occurs through aggregation of groups of hydrophobic segments, which results from their mutual attraction.

The monomers from which block copolymers are made generally include polymer chains. Under the terminology used here, these monomers may be referred to as macromonomers. Likewise, the corresponding elements in the formed block copolymer can be referred to as macro-mers.

A hydrophobic polymer chain can be, for example, a polyolefin, preferably an olefin having 4 to about 12 carbon atoms as in poly(isobutylene), or a polysiloxane, such as poly(dimethylsiloxane). A hydrophilic polymer chain can be, for example, a poly(alkylene glycol), such as polyethylene glycol, a polyacrylate, such as polymers of methacrylate, 2-hydroxyethyl methylmethacrylate, or an aminoalkyl acrylate, such as N,N-dimethylacrylamide.

A preferred amphiphilic block copolymer network comprises macromolecular mers of polyethylene glycol (PEG), poly(isobutylene) (PIB), and poly(dimethylsiloxane) (PDMS). The polymer network can be synthesized by hydrosilation of allyl-terminated macromolecular monomers with pentamethylcyclopentasiloxane in toluene. The pore size of this network can be controlled by controlling the molecular weight of the hydrophilic macro-monomers. The strength can be controlled by the lengths of the hydrophobic macro-monomers and by the crosslink density. PDMS is oxyphilic and enhances transport of oxygen and related substances through the network.

More generally, macro-monomers, each a hydrophilic or hydrophobic polymer chain with functional end caps, can be polymerized together to form an amphiphilic block copolymer network. Suitable end caps include, for example, organic polyisocyanates, such as tolyene diisocyanate and diphenylmethane diisocyanate, acrylate, methacrylate and styryl groups. Block copolymers networks can also be generated by polymerizing polymer chains with monomers, for example, methacrylol capped PIB with dimethylaminoethyl methacrylate.

The solubility difference between hydrophobic and hydrophilic monomers can present difficulties during synthesis of amphiphilic block copolymers. One approach to overcoming this difficulty is to use a removable blocking agent to make a hydrophobic monomer temporarily hydrophilic or a hydrophilic monomer temporarily hydrophobic. For example a hydrophobic tertiary amine or amide can be made hydrophilic with a protonating blocking agent. For another example, a hydrophilic methacrylate can be made hydrophobic by the blocking agent trimethylsilyl chloride. The trimethylsilyl chloride can be removed by swelling the polymer in a 5% hydrochloric acid solution.

Amphiphilic block copolymers as used in the invention are generally biostable. However, bioerodable amphiphilic block copolymers can also be designed. For example, a bioerodable amphiphilic block copolymer can be obtained by copolymerizing, under free radical conditions, styrene-telechelic PIB's with vinyl acetate.

The amphiphilic block copolymer coating can be applied to the graft by any suitable means, including for example, spray coating, dip coating, and brush coating. In one embodiment, the graft is spin coated. Spin coating involves placing the graft with the copolymer constituents in a cylindircal tube. The tube is spun, whereby the macromonomers distribute evenly about the graft along the perimeter of the tube. With the tube, spinning, the polymerization and/or crosslinking reactions are initiated.

The polymer carries a drug of a type, in a manner, and in an amount sufficient to significantly inhibit thrombosis and/or stenosis. The exemplary graft delays the onset of or reduces the occurrence of one or more of these conditions to a statically significant degree in comparison to an otherwise equivalent graft without the drug. The drug can be, for example, cytostatic or cytotoxic.

A graft according to the invention can be used to deliver virtually any drug, including without limitation, hydrophilic compounds, hydrophobic compounds, metal compounds, salts, polymers, antibodies, proteins, nucleic acids, and cells. It is further possible, with simple variations in the amphiphilic block copolymer composition, to control the release rate of any of these drugs.

Diverse drugs are of interest in connection with thrombosis and/or stenosis, including the following:

anticoagulants, including heparin, low molecular weight herapins, hirudin, warfarin, bivalirudin, and Vasoflux;

antithrombotic agents, including argatroban, efegatran, tick anticoagulant peptide, Ppack, HMG-CoA reductase inhibitors, thromboxane A2 receptor inhibitors, endothelium-derived relaxing factor plasminogen activator inhibitor, tissue-type plasminogen activator (tPA), ReoPro, fibrin and fibrin peptide A, chrysalin, D-Phe-ProArg chloromethyl ketone, and glycoprotein IIb/IIIa receptor inhibitors (including, abciximab, eptifibatide, tirofiban, lamifiban, fradafiban, cromafiban, toxifiban, XV454, lefradafiban, klerval, lotrafiban, orbofiban, and xemilofiban)

antiplatelet agents, including aspirin, dipyridamole, apo-dipyridamole, persantine, prostacyclin, ticlopidine, clopidogrel, cromafiban, and cilostazol;

antiproliferative agents, including triazolopyrimidine (Trapidil), paclitaxel (Taxol), tranilast (Rizaben), Rapamycin (sirolimus), tacrolimus, angiopeptin, butyrate, ceramide, ciprostene, cultrazine, cyclosporine, EGF-genistein, fucoidans, halofuginone, lioprost, ketaserine, predisone, dipyridamole, 17-beta-estradiol, suramin, nitric oxide donors (including FK409, linsidomine, and molsidomine), phytoestrogens, colchine, probucol, terbinafine, etoposide, doxorubicine, beraprost sodium, Resten-NG, actinomycin D, phosphorylcholine, Batimastat, and calcium channel blockers (including, amlodipine, verapamil, diltiazem HCL, and nifedipine);

anti-inflammatory agents, including dipyridamole, and glucocorticoids (including betamethazone, rosiglitazone, and dexamethazone);

lipid-lowering drugs, including omega-3 fatty acids, prostaglandin $I_2$, prostaglandin E1, pravastatin, lovastatin, cerivastatin, fluvastatin, and simvastatin;

specific growth factor antagonists, including lanreotide;

antioxidants, including alpha-tocopherol, beta-carotene, and probucol;

genetic materials, including those carried by viral vectors, plasmids, and lipid-based carriers (including, antisense oligonucleotides such as AVI-2221, INX-3280, RestenASE), ribosymes, and cytochalasin B;

angiogenic growth factors, including platelet derived growth factors alpha and beta;

antihypertension drugs, including angiotensin converting enzyme inhibitors and angiotensin II receptor antagonists (including captopril, quinapril, cilazapril, losartan, and valsartan)

radioactive compounds, including metal salts;

lymphokines including (IL)-1, -2, -3, and -4, as well as colony stimulating factors such as G-CSF, GM-CSF, and M-CSF.

Most of these drugs have analogs and derivative that are also of interest in preventing stenosis and/or thrombosis. Analogs and derivatives include minor alterations in structure and substitutions or additions of atoms or functional groups that do not alter, except perhaps by degree, the primary mechanism of action. For example paclitaxel derivatives include, without limitation, taxotere, baccatin, 10-deacetyltaxol, 7-xylosyl-10-deacetyltaxol, cephalomannine, 10-deacetyl-7-epitaxol, 7 epitaxol, 10-deacetylbaccatin III, and 10-deacetylcephaolmannine.

Virtually any of the drugs of interest in preventing stenosis and/or thrombosis can be delivered using an amphiphilic block copolymer on a graft according to the present invention. A preferred graft/polymer combination can deliver many of these drugs with little or no variation in the polymer composition. For example, amphiphilic block copolymer networks, such as networks comprising PEG, PIB, and PDMS, can be used to deliver with a controlled release rate any of triazolopyrimidine, paclitaxol, and sirolimus on the one hand and any of stem cells, antibodies, genetic materials, and lymphokines on the other. Where some variation is required to achieve appropriate release rates for these various drugs or drug groups, it is preferred that these variations be limited to the ratios and/or chain lengths of the macromonomers and the degree of crosslinking.

The polymer can be loaded with the drug by any suitable means. One approach is to include the drug with the macromonomers as they are polymerized together. Another is to dissolve the drug in a solvent and swell the polymer with the solvent. All or part of the solvent can be evaporated and the polymer swelled again to increase the drug loading level.

The drug can remain in the graft, as when the drug is a radiation source. More generally, however it is preferred that the drug be released by the graft, either to be absorbed in tissues around the graft or to be released into the blood stream. In one embodiment, the drug is of a type that can absorb and be stored in living tissues.

An advantage of the present invention is that amphiphilic block copolymer networks can be tailored to provide virtually any desired release rate. Non-soluble amphiphilic block copolymers generally provide release rate kinetics in the range from about 0.4 order to about first order. Within this framework, a particular release rate may be targeted. In one embodiment, the graft can release from about 10 to about 90 percent of the drug within the first thirty days of installation, preferably from about 20 to about 60 percent of the drug within the first thirty days. In another embodiment, the graft releases from about 10 to about 90 percent of the drug within the first six hours of installation, preferably from about 20 to about 60 percent of the drug within the first six hours.

In one embodiment of the invention, two surfaces of the graft have two different drug/polymer combinations and release drugs at two different rates. For example, the inner surface of the graft can be coated with a polymer carrying a first drug that is released into the blood stream, whereas the outer surface can be coated with another the same or a different polymer carrying a second drug that releases into tissues surrounding the graft.

A variety of options are available for controlling the release rate. The release rate can be varied though any of: the identity of the macro-monomers, the lengths of the macro-monomer chains, the ratios of the macro-monomers, the degree of crosslinking in the copolymer network, the loading of the drug, and the thickness of the amphiphilic polymer coating. Additional release patterns can be obtained by employing multi-layer coatings, which may include layers that are not amphiphilic block copolymers. For example, a barrier layer may be formed over the amphiphilic block copolymer to slow the release rate. One of the biocompatible coatings listed above would be appopriate for a barrier coating. A preferred barrier layer comprises parylene or a derivative thereof.

A further advantage of the amphiphilic block copolymer of the present invention is that its pore structure can be easily controlled. Controlled porosity is of value in grafts for purposes in addition to controlling release rates. A porous inner surface is desireable to promote endothelialization. A porous outer surface is desireable to promote ingrowth of tissue. An overall low permeabilty is desirable to prevent blood leakage. An amphiphilic block copolymer can be optimized to any of these functions with minimal changes in chemical properties.

FIG. 1 illustrates the possible locations and functions for an amphiphilic block copolymer coating a surface of the wall of a graft. The Figure shows a graft 10 with five layers of polymer coating a fabric wall 12. Although the five layer structure shown is within the scope of the invention, it is not contemplated that so many different layers will be required for a given application. Depending on the drug or drugs used, the desired release rates, and the desired pore structures for the inner and outer layers (which may change as further research is carried out to determine what pore structures are optimal for these layers), the functions of two or more layers, in some cases all of the layers, can be served by a single coating.

Inner layer 14 has a pore structure optimized for endothelialization. Layer 16 provides controlled release for a drug that releases at least into the lumen formed by the wall 12. Layer 18 can limit the permeation of blood through the graft. Layer 18 can also be a barrier layer for a drug. Layer 20 provides controlled release of a drug at least into the tissues surrounding the graft 10. Layer 22 has a pore stucture optimized for tissue ingrowth. The inner and outer layers typically have a mean pore size in the range from about 1 to about 100 micrometers, preferably from about 10 to about 50 micrometers.

In the exemplary embodiment of the invention, at least one of the layers 16 and 20 includes an amphiphilic block copolymer. Typically, the amphiphilic block copolymer layer will provide the functions of two or more layers in the graft 10. In one embodiment, one amphiphilic block copolymer layer serves all the functions of the five layers of the graft 10. In another embodiment, two amphiphilic block copolymer layers, differing in some quality, serve the functions of two or more layers of the graft 10. Each of the five layers 14, 16, 18, 20, and 22 is considered to coat a surface of the wall 12, although one or more of these layers may be separated from the wall 12 by one or more other layers.

Local drug delivery through a graft coating often allows the use of higher drug concentrations in those locations where the drug is needed than could safely be achieved with system wide delivery. Nonetheless, there can be synergy between graft-based delivery and system-wide delivery. Thus, in one embodiment, treatment with a drug-coated graft according to the invention is combined with oral or intravenous dosage of the same drug.

An amphiphilic block copolymer network has unique advantages for drug-coated grafts. Nonetheless, in certain situations, collagen can be used as an alternative. As a graft coating, collagen can smooth over surfaces and create bio- and hemo-compatibility. In one embodiment, a graft with a carpet like surface is coated with collagen. Preferably, the collagen contains either stem cells, antibodies, genetic materials, or lymphokines in an amount to significantly inhibit thrombosis and/or stenosis. Of particular interest in this group are stem cells and GM-CSF.

In addition to a graft coating, an amphiphilic block copolymer network can be used to form microparticles. Such microparticles can also carry and deliver at a controlled rate a wide range of drugs. Microparticles have a size range from about 10 nanometers to about 10 micrometers.

One aspect of the invention relates to the use of microparticles, especially amphiphilic block copolymer microparticles, to carry a drug that inhibits thrombosis and/or stenosis. The microparticles can be distributed in a coating on a graft. The coating can be a polymer, either biostable or bioerodable. In a preferred embodiment, the coating containing the microparticles is a hydrogel. A hydrogel can be synthetic polymer, such as polymalic acid, polyamino acids, polyacrylic acids, polyalkylene glycol (e.g., polyethylene glycol), polyalkyene oxide (e.g. polyethylene oxide), polyvinylpyrrolidone, polyester, polyvinyl alcohols, and hydrophilic polyurethanes, polyglutarunic acid, poly 2-hydroxyethyl methacrylate (PHEMA). Additional examples of hydrogels include collagen, NO-carboxymethyl chitosan (NOCC), albumin, gelatin, starch, celluloses, dextran, polymalic acid, polyamino acids and their co-polymers or lightly cross-linked forms, polysaccharides and their derivatives, sodium alginate, karaya gum, gelatin, guar gum, agar, algin, carrageenans, pectin, locust bean gums, xanthan, starch-based gums, hydroxyalkyl and ethyl ethers of cellulose, sodium carboxymethylcellulose. Alternative, the microparticles can be distributed around the graft during or shortly after installation.

The invention has been shown and described with respect to certain aspects, examples, and embodiments. While a particular feature of the invention may have been disclosed with respect to only one of several aspects, examples, or embodiments, the feature may be combined with one or more other features of the other aspects, examples, or embodiments as may be advantageous for any given or particular application. Furthermore, to the extent that the term "includes" is used in either the detailed description or the claims, the term is intended to be inclusive in the manner of the term "comprising."

The invention claimed is:

1. A flexible vascular graft for connecting to a blood vessel, said vascular graft comprising a flexible wall that forms a passageway for blood flow through the vascular graft, a first drug layer at least partially coated on an inner surface of said flexible wall and an inner layer, said inner layer formed of a porous material designed to promote endothelialization, said first drug layer including at least one drug and a flexible and substantially biologically inert amphiphilic block copolymer, said amphiphilic block copolymer having a structure that controllably releases up to about 90 percent of at least one of said drugs into said inner layer within about thirty days of being connected to the blood vessel, said amphiphilic block copolymer including a network including both hydrophobic and hydrophilic polymer chains that can swell in both hydrophobic and hydrophilic solvents, said at least one drug formulated to inhibit stenosis, vascular narrowing, thrombosis or combinations thereof, and a barrier layer to inhibit release of at least one of said drugs from said first drug layer into said inner layer.

2. The flexible vascular graft as defined in claim 1, wherein said flexible wall includes a biostable fabric material, said biostable fabric material including a material selected from the group consisting of polyester, polytetrafluoroethylene, polyurethane, polysilicones, poly(meth)acrylates, polyalkyl oxides, polyvinyl alcohols, polyalkylene glycols, polyvinyl pyrrolidone or combinations thereof.

3. The flexible vascular graft as defined in claim 2, wherein said amphiphilic block copolymer includes macromolecular mers of polyethylene glycol, poly(isobutylene), and poly(dimethylsiloxane).

4. The flexible vascular graft as defined in claim 3, wherein said inner layer includes collagen.

5. The flexible vascular graft as defined in claim 4, wherein the drug in said first drug layer includes trapidil and GM-CSF.

6. The flexible vascular graft as defined in claim 5, including a barrier layer to inhibit release of at least one of said drugs from said first drug layer into said inner layer, said baffler layer including parylene or a derivative thereof.

7. The flexible vascular graft as defined in claim 6, including a first penetration baffler layer to inhibit penetration of blood through said vascular graft.

8. The flexible vascular graft as defined in claim 7, including a second drug layer positioned on said vascular graft to release at least one drug into tissues surrounding said vascular graft.

9. The flexible vascular graft as defined in claim 1, wherein said amphiphilic block copolymer includes macromolecular mers of polyethylene glycol, poly(isobutylene), and poly(dimethylsiloxane).

10. The flexible vascular graft as defined in claim 1, wherein said inner layer includes collagen.

11. The flexible vascular graft as defined in claim 1, wherein the drug in said first drug layer includes trapidil and GM-CSF.

12. The flexible vascular graft as defined in claim 1, including a barrier layer to inhibit release of at least one of said drugs from said first drug layer into said inner layer, said barrier layer including parylene or a derivative thereof.

13. The flexible vascular graft as defined in claim 1, wherein said amphiphilic block copolymer has a structure that controllably releases up to about 90 percent of at least one of said drugs from said first drug layer into said inner layer within about six hours of being connected to the blood vessel.

14. The flexible vascular graft as defined in claim 1, including a first penetration baffler layer to inhibit penetration of blood through said vascular graft.

15. The flexible vascular graft as defined in claim 1, including a second drug layer positioned on said vascular graft to release at least one drug into tissues surrounding said vascular graft.

16. The flexible vascular graft as defined in claim 15, wherein at least one drug in said second drug layer is not included in said first drug layer.

17. The flexible vascular graft as defined in claim 15, including a drug barrier layer to inhibit release of at least one drug from said second drug layer.

18. The flexible vascular graft as defined in claim 16, including a drug barrier layer to inhibit release of at least one drug from said second drug layer.

19. A stent for insertion into a blood vessel, said stent comprising an expandable wall structure that forms a passageway for blood flow through the stent, a first drug layer at least partially coated on said expandable wall structure and an inner layer, said inner layer formed of a porous material designed to promote endothelialization, said first drug layer including at least one drug and a substantially biologically inert amphiphilic block copolymer, said amphiphilic block copolymer having a structure that controllably releases up to about 90 percent of at least one of said drugs into said inner layer within about thirty days of being inserted in the blood vessel, said amphiphilic block copolymer including a network including both hydrophobic and hydrophilic polymer chains that can swell in both hydrophobic and hydrophilic solvents, said amphiphilic block copolymer includes macromolecular mers of polyethylene glycol, poly(isobutylene), and poly(dimethylsiloxane), said at least one drug formulated to inhibit stenosis, vascular narrowing, thrombosis or combinations thereof.

20. The stent as defined in claim 19, wherein said inner layer includes collagen.

21. The stent as defined in claim 19, wherein said inner layer includes collagen.

22. The stent as defined in claim 21, wherein the drug in said first drug layer includes trapidil and GM-CSF.

23. The stent as defined in claim 22, including a barrier layer to inhibit release of at least one of said drugs from said first drug layer into said inner layer, said barrier layer including parylene or a derivative thereof.

24. The stent as defined in claim 23, including a first penetration barrier layer to inhibit penetration of blood through said stent.

25. The stent as defined in claim 24, including a second drug layer positioned on said stent.

26. The stent as defined in claim 19, wherein the drug in said first drug layer includes trapidil and GM-CSF.

27. The stent as defined in claim 19, including a barrier layer to inhibit release of at least one of said drugs from said first drug layer into said inner layer, said barrier layer including parylene or a derivative thereof.

28. The stent as defined in claim 19, wherein said amphiphilic block copolymer having a structure that controllably releases up to about 90 percent of at least one of said drugs from said first drug layer into said inner layer within about six hours of being connected to the blood vessel.

29. The stent as defined in claim 19, including a first penetration barrier layer to inhibit penetration of blood through said stent.

30. The stent as defined in claim 19, including a second drug layer positioned on said stent.

31. The stent as defined in claim 30, wherein at least one drug in said second drug layer is not included in said first drug layer.

32. The stent as defined in claim 30, including a drug barrier layer to inhibit release of at least one drug from said second drug layer.

33. The stent as defined in claim 19, wherein teeth or other indentations that are part of a ratcheting mechanism.

34. A method for repairing a blood vessel comprising:
a. providing a graft for connection to or insertion into a blood vessel, said graft comprising a wall that forms a passageway for blood flow through the graft, a first drug layer at least partially coated on said wall and an inner layer, said inner layer formed of a porous material designed to promote endothelialization, said first drug layer including at least one drug and a flexible and substantially biologically inert amphiphilic block copolymer, said amphiphilic block copolymer including a network including both hydrophobic and hydrophilic polymer chains that can swell in both hydrophobic and hydrophilic solvents, said amphiphilic block copolymer includes macromolecular mers of polyethylene glycol, poly(isobutylene), and poly(dimethylsiloxane), said at least one drug formulated to inhibit stenosis, vascular narrowing, thrombosis or combinations thereof;
b. connecting said graft to or inserting said graft in the blood vessel; and,
c. controllably releasing up to about 90 Percent of at least one of said drugs into said blood vessel within about thirty days of being connected to or inserted in the blood vessel.

35. The method as defined in claim 34, wherein said graft is a stent.

36. The method as defined in claim 35, wherein said stent includes teeth or other indentations, and including the step of using a ratcheting mechanism to expand said stent in said blood vessel.

37. The method as defined in claim 34, wherein said graft is a vascular graft that includes a flexible wall, said flexible wall includes a biostable fabric material, said biostable fabric material including a material selected from the group consisting of polyester, polytetrafluoroethylene, polyurethane, polysilicones, poly(meth)acrylates, polyalkyl oxides, polyvinyl alcohols, polyalkylene glycols, polyvinyl pyrrolidone or combinations thereof.

38. The method as defined in claim 37, wherein said inner layer includes collagen.

39. The method as defined in claim 38, wherein the drug in said first drug layer includes trapidil and GM-CSF.

40. The method as defined in claim 39, including a barrier layer to inhibit release of at least one of said drugs from said first drug layer into said inner layer, said barrier layer including parylene or a derivative thereof.

41. The method as defined in claim 40, wherein up to about 90 percent of at least one of said drugs is released into said blood vessel within about six hours of being connected to or inserted into the blood vessel.

42. The method as defined in claim 41, wherein said graft includes a first penetration barrier layer to inhibit penetration of blood through said graft.

43. The method as defined in claim 41, wherein said graft includes a second drug layer.

44. The method as defined in claim 34, wherein said inner layer includes collagen.

45. The method as defined in claim 34, wherein the drug in said first drug layer includes trapidil and GM-CSF.

46. The method as defined in claim 34, including a barrier layer to inhibit release of at least one of said drugs from said first drug layer into said inner layer, said barrier layer including parylene or a derivative thereof.

47. The method as defined in claim 34, wherein up to about 90 percent of at least one of said drugs is released into said blood vessel within about six hours of being connected to or inserted into the blood vessel.

48. The method as defined in claim 34, wherein said graft includes a first penetration barrier layer to inhibit penetration of blood through said graft.

49. The method as defined in claim 34, wherein said graft includes a second drug layer.

50. The method as defined in claim 49, including the step of releasing at least one drug from said second drug layer into tissues surrounding said graft.

51. The method as defined in claim 49, wherein at least one drug in said second drug layer is not included in said first drug layer.

52. The method as defined in claim 49, wherein said graft includes a drug barrier layer to inhibit release of at least one drug from said second drug layer.

53. The method as defined in claim 34, wherein at least one of said drugs in said first drug layer is at least partially contained in microparticles of said amphiphilic block copolymer, said microparticles having a size of up to about 10 micrometers.

54. The method as defined in claim 53, wherein said microparticles of said amphiphilic block copolymer are at least partially dispersed in hydrogel.

55. The method as defined in claim 34, including the step of administering at least one drug to the patient either orally or intravenously.

* * * * *